United States Patent
Debreczeny (10) Patent No.: US 8,068,891 B2
(45) Date of Patent: Nov. 29, 2011

(54) SYMMETRIC LED ARRAY FOR PULSE OXIMETRY

(75) Inventor: Martin P. Debreczeny, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1430 days.

(21) Appl. No.: 11/541,287

(22) Filed: Sep. 29, 2006

(65) Prior Publication Data

US 2008/0081972 A1    Apr. 3, 2008

(51) Int. Cl.
*A61B 5/1455* (2006.01)

(52) U.S. Cl. .................. 600/323; 600/322; 600/324

(58) Field of Classification Search ........... 600/309–344
See application file for complete search history.

(56) References Cited

U.S. PATENT DOCUMENTS

| | | |
|---|---|---|
| 3,638,640 A | 2/1972 | Shaw |
| 3,721,813 A | 3/1973 | Condon et al. |
| 3,910,701 A * | 10/1975 | Henderson et al. ........... 600/322 |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |

(Continued)

FOREIGN PATENT DOCUMENTS

CA    2494030    2/2004

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur
*Assistant Examiner* — Chu Chuan (JJ) Liu
(74) *Attorney, Agent, or Firm* — Fletcher Yoder (57) ABSTRACT

There is provided a sensor for pulse oximeter systems. The sensor comprises a first source of electromagnetic radiation configured to operate at a first wavelength, a second source of electromagnetic radiation configured to operate at a second wavelength, and a third source of electromagnetic radiation configured to operate at a third wavelength. The emission spectra of the first and third sources of electromagnetic radiation overlap at their half power level or greater and correspond to a center wavelength in the range of 650 to 670 nm.

20 Claims, 4 Drawing Sheets

U.S. PATENT DOCUMENTS

| | | | |
|---|---|---|---|
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,539 A | 8/1991 | Hattori et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A * | 4/1993 | Takatani et al. ............... 600/334 |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A * | 6/1993 | Rosenthal ............... 250/341.1 |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A * | 4/1994 | Hatschek ............... 600/323 |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |

| | | | | | | |
|---|---|---|---|---|---|---|
| 5,429,129 A | 7/1995 | Lovejoy et al. | | 5,713,355 A | 2/1998 | Richardson et al. |
| 5,431,159 A | 7/1995 | Baker et al. | | 5,724,967 A | 3/1998 | Venkatachalam |
| 5,431,170 A | 7/1995 | Mathews | | 5,727,547 A | 3/1998 | Levinson et al. |
| 5,437,275 A | 8/1995 | Amundsen et al. | | 5,730,124 A | 3/1998 | Yamauchi |
| 5,438,986 A | 8/1995 | Disch et al. | | 5,731,582 A | 3/1998 | West |
| 5,448,991 A | 9/1995 | Polson et al. | | D393,830 S | 4/1998 | Tobler et al. |
| 5,452,717 A | 9/1995 | Branigan et al. | | 5,743,260 A | 4/1998 | Chung et al. |
| 5,465,714 A | 11/1995 | Scheuing | | 5,743,263 A | 4/1998 | Baker, Jr. |
| 5,469,845 A | 11/1995 | DeLonzor et al. | | 5,746,206 A | 5/1998 | Mannheimer |
| RE35,122 E | 12/1995 | Corenman et al. | | 5,746,697 A | 5/1998 | Swedlow et al. |
| 5,482,034 A | 1/1996 | Lewis et al. | | 5,752,914 A | 5/1998 | DeLonzor et al. |
| 5,482,036 A | 1/1996 | Diab et al. | | 5,755,226 A | 5/1998 | Carim et al. |
| 5,483,646 A | 1/1996 | Uchikoga | | 5,758,644 A | 6/1998 | Diab et al. |
| 5,485,847 A | 1/1996 | Baker, Jr. | | 5,760,910 A | 6/1998 | Lepper, Jr. et al. |
| 5,490,505 A | 2/1996 | Diab et al. | | 5,766,125 A | 6/1998 | Aoyagi et al. |
| 5,490,523 A | 2/1996 | Isaacson et al. | | 5,766,127 A | 6/1998 | Pologe et al. |
| 5,491,299 A | 2/1996 | Naylor et al. | | 5,769,785 A | 6/1998 | Diab et al. |
| 5,494,032 A | 2/1996 | Robinson et al. | | 5,772,587 A | 6/1998 | Gratton et al. |
| 5,497,771 A | 3/1996 | Rosenheimer | | 5,774,213 A | 6/1998 | Trebino et al. |
| 5,499,627 A | 3/1996 | Steuer et al. | | 5,776,058 A | 7/1998 | Levinson et al. |
| 5,503,148 A | 4/1996 | Pologe et al. | | 5,776,059 A | 7/1998 | Kaestle |
| 5,505,199 A | 4/1996 | Kim | | 5,779,630 A | 7/1998 | Fein et al. |
| 5,507,286 A | 4/1996 | Solenberger | | 5,779,631 A | 7/1998 | Chance |
| 5,517,988 A | 5/1996 | Gerhard | | 5,782,237 A | 7/1998 | Casciani et al. |
| 5,520,177 A | 5/1996 | Ogawa et al. | | 5,782,756 A | 7/1998 | Mannheimer |
| 5,521,851 A | 5/1996 | Wei et al. | | 5,782,758 A | 7/1998 | Ausec et al. |
| 5,522,388 A | 6/1996 | Ishikawa et al. | | 5,786,592 A | 7/1998 | Hök |
| 5,524,617 A | 6/1996 | Mannheimer | | 5,790,729 A | 8/1998 | Pologe et al. |
| 5,529,064 A | 6/1996 | Rall et al. | | 5,792,052 A | 8/1998 | Isaacson et al. |
| 5,533,507 A | 7/1996 | Potratz et al. | | 5,795,292 A | 8/1998 | Lewis et al. |
| 5,551,423 A | 9/1996 | Sugiura | | 5,797,841 A | 8/1998 | DeLonzor et al. |
| 5,551,424 A | 9/1996 | Morrison et al. | | 5,800,348 A | 9/1998 | Kaestle |
| 5,553,614 A | 9/1996 | Chance | | 5,800,349 A | 9/1998 | Isaacson et al. |
| 5,553,615 A | 9/1996 | Carim et al. | | 5,803,910 A | 9/1998 | Potratz |
| 5,555,882 A | 9/1996 | Richardson et al. | | 5,807,246 A | 9/1998 | Sakaguchi et al. |
| 5,558,096 A | 9/1996 | Palatnik | | 5,807,247 A | 9/1998 | Merchant et al. |
| 5,560,355 A | 10/1996 | Merchant et al. | | 5,807,248 A | 9/1998 | Mills |
| 5,564,417 A | 10/1996 | Chance | | 5,810,723 A | 9/1998 | Aldrich |
| 5,575,284 A | 11/1996 | Athan et al. | | 5,810,724 A | 9/1998 | Gronvall |
| 5,575,285 A | 11/1996 | Takanashi et al. | | 5,813,980 A | 9/1998 | Levinson et al. |
| 5,577,500 A | 11/1996 | Potratz | | 5,817,008 A | 10/1998 | Rafert et al. |
| 5,582,169 A | 12/1996 | Oda et al. | | 5,817,009 A | 10/1998 | Rosenheimer et al. |
| 5,584,296 A | 12/1996 | Cui et al. | | 5,817,010 A | 10/1998 | Hibl |
| 5,588,425 A | 12/1996 | Sackner et al. | | 5,818,985 A | 10/1998 | Merchant et al. |
| 5,588,427 A | 12/1996 | Tien | | 5,820,550 A | 10/1998 | Polson et al. |
| 5,590,652 A | 1/1997 | Inai | | 5,823,950 A | 10/1998 | Diab et al. |
| 5,595,176 A | 1/1997 | Yamaura | | 5,823,952 A | 10/1998 | Levinson et al. |
| 5,596,986 A | 1/1997 | Goldfarb | | 5,827,182 A | 10/1998 | Raley et al. |
| 5,611,337 A | 3/1997 | Bukta | | 5,830,135 A | 11/1998 | Bosque et al. |
| 5,617,852 A | 4/1997 | MacGregor | | 5,830,136 A | 11/1998 | DeLonzor et al. |
| 5,619,992 A | 4/1997 | Guthrie et al. | | 5,830,137 A | 11/1998 | Scharf |
| 5,626,140 A | 5/1997 | Feldman et al. | | 5,830,139 A | 11/1998 | Abreu |
| 5,630,413 A | 5/1997 | Thomas et al. | | 5,833,603 A * | 11/1998 | Kovacs et al. ................. 600/317 |
| 5,632,272 A | 5/1997 | Diab et al. | | 5,839,439 A | 11/1998 | Nierlich et al. |
| 5,632,273 A | 5/1997 | Suzuki | | RE36,000 E | 12/1998 | Swedlow et al. |
| 5,634,459 A | 6/1997 | Gardosi | | 5,842,979 A | 12/1998 | Jarman et al. |
| 5,638,593 A | 6/1997 | Gerhardt et al. | | 5,842,981 A | 12/1998 | Larsen et al. |
| 5,638,818 A | 6/1997 | Diab et al. | | 5,842,982 A | 12/1998 | Mannheimer |
| 5,645,059 A | 7/1997 | Fein et al. | | 5,846,190 A | 12/1998 | Woehrle |
| 5,645,060 A | 7/1997 | Yorkey | | 5,851,178 A | 12/1998 | Aronow |
| 5,645,440 A | 7/1997 | Tobler et al. | | 5,851,179 A | 12/1998 | Ritson et al. |
| 5,660,567 A | 8/1997 | Nierlich et al. | | 5,853,364 A | 12/1998 | Baker, Jr. et al. |
| 5,662,105 A | 9/1997 | Tien | | 5,860,919 A | 1/1999 | Kiani-Azarbayjany et al. |
| 5,662,106 A | 9/1997 | Swedlow et al. | | 5,865,736 A | 2/1999 | Baker, Jr. et al. |
| 5,666,952 A | 9/1997 | Fuse et al. | | 5,871,442 A | 2/1999 | Madarasz et al. |
| 5,671,529 A | 9/1997 | Nelson | | 5,873,821 A | 2/1999 | Chance et al. |
| 5,673,692 A | 10/1997 | Schulze et al. | | 5,879,294 A | 3/1999 | Anderson et al. |
| 5,673,693 A | 10/1997 | Solenberger | | 5,885,213 A | 3/1999 | Richardson et al. |
| 5,676,139 A | 10/1997 | Goldberger et al. | | 5,890,929 A | 4/1999 | Mills et al. |
| 5,676,141 A | 10/1997 | Hollub | | 5,891,021 A | 4/1999 | Dillon et al. |
| 5,678,544 A | 10/1997 | DeLonzor et al. | | 5,891,022 A | 4/1999 | Pologe |
| 5,680,857 A | 10/1997 | Pelikan et al. | | 5,891,024 A | 4/1999 | Jarman et al. |
| 5,685,299 A | 11/1997 | Diab et al. | | 5,891,025 A | 4/1999 | Buschmann et al. |
| 5,685,301 A | 11/1997 | Klomhaus | | 5,891,026 A | 4/1999 | Wang et al. |
| 5,687,719 A | 11/1997 | Sato et al. | | 5,902,235 A | 5/1999 | Lewis et al. |
| 5,687,722 A | 11/1997 | Tien et al. | | 5,910,108 A | 6/1999 | Solenberger |
| 5,692,503 A | 12/1997 | Kuenstner | | 5,911,690 A | 6/1999 | Rall |
| 5,692,505 A | 12/1997 | Fouts | | 5,912,656 A | 6/1999 | Tham et al. |
| 5,709,205 A | 1/1998 | Bukta | | 5,913,819 A | 6/1999 | Taylor et al. |

| | | | | | | |
|---|---|---|---|---|---|---|
| 5,916,154 A | 6/1999 | Hobbs et al. | | 6,154,667 A | 11/2000 | Miura et al. |
| 5,916,155 A | 6/1999 | Levinson et al. | | 6,157,850 A | 12/2000 | Diab et al. |
| 5,919,133 A | 7/1999 | Taylor et al. | | 6,163,175 A | 12/2000 | Sharpe-Geisler |
| 5,919,134 A | 7/1999 | Diab | | 6,163,715 A | 12/2000 | Larsen et al. |
| 5,920,263 A | 7/1999 | Huttenhoff et al. | | 6,165,005 A | 12/2000 | Mills et al. |
| 5,921,921 A | 7/1999 | Potratz et al. | | 6,173,196 B1 | 1/2001 | Delonzor et al. |
| 5,922,607 A | 7/1999 | Bernreuter | | 6,178,343 B1 | 1/2001 | Bindszus et al. |
| 5,924,979 A | 7/1999 | Swedlow et al. | | 6,181,958 B1 | 1/2001 | Steuer et al. |
| 5,924,980 A | 7/1999 | Coetzee | | 6,181,959 B1 | 1/2001 | Schöllermann et al. |
| 5,924,982 A | 7/1999 | Chin | | 6,184,521 B1 | 2/2001 | Coffin, IV et al. |
| 5,924,985 A | 7/1999 | Jones | | 6,188,470 B1 | 2/2001 | Grace |
| 5,934,277 A | 8/1999 | Mortz | | 6,192,260 B1 | 2/2001 | Chance |
| 5,934,925 A | 8/1999 | Tobler et al. | | 6,192,261 B1 | 2/2001 | Gratton et al. |
| 5,940,182 A | 8/1999 | Lepper, Jr. et al. | | 6,195,575 B1 | 2/2001 | Levinson |
| 5,954,644 A | 9/1999 | Dettling et al. | | 6,198,951 B1 | 3/2001 | Kosuda et al. |
| 5,960,610 A | 10/1999 | Levinson et al. | | 6,206,830 B1 | 3/2001 | Diab et al. |
| 5,961,450 A | 10/1999 | Merchant et al. | | 6,213,952 B1 | 4/2001 | Finarov et al. |
| 5,961,452 A | 10/1999 | Chung et al. | | 6,217,523 B1 | 4/2001 | Amano et al. |
| 5,964,701 A | 10/1999 | Asada et al. | | 6,222,189 B1 | 4/2001 | Misner et al. |
| 5,971,930 A | 10/1999 | Elghazzawi | | 6,226,539 B1 | 5/2001 | Potratz |
| 5,978,691 A | 11/1999 | Mills | | 6,226,540 B1 | 5/2001 | Bernreuter |
| 5,978,693 A | 11/1999 | Hamilton et al. | | 6,229,856 B1 | 5/2001 | Diab et al. |
| 5,983,122 A | 11/1999 | Jarman et al. | | 6,230,035 B1 | 5/2001 | Aoyagi et al. |
| 5,987,343 A | 11/1999 | Kinast | | 6,233,470 B1 | 5/2001 | Tsuchiya |
| 5,991,648 A | 11/1999 | Levin | | 6,236,871 B1 | 5/2001 | Tsuchiya |
| 5,995,855 A | 11/1999 | Kiani et al. | | 6,236,872 B1 | 5/2001 | Diab et al. |
| 5,995,856 A | 11/1999 | Mannheimer et al. | | 6,240,305 B1 | 5/2001 | Tsuchiya |
| 5,995,858 A | 11/1999 | Kinast | | 6,253,097 B1 | 6/2001 | Aronow et al. |
| 5,995,859 A | 11/1999 | Takahashi | | 6,253,098 B1 | 6/2001 | Walker et al. |
| 5,997,343 A | 12/1999 | Mills et al. | | 6,256,523 B1 | 7/2001 | Diab et al. |
| 5,999,834 A | 12/1999 | Wang et al. | | 6,256,524 B1 | 7/2001 | Walker et al. |
| 6,002,952 A | 12/1999 | Diab et al. | | 6,261,236 B1 | 7/2001 | Grimblatov |
| 6,005,658 A | 12/1999 | Kaluza et al. | | 6,263,221 B1 | 7/2001 | Chance et al. |
| 6,006,120 A | 12/1999 | Levin | | 6,263,222 B1 | 7/2001 | Diab et al. |
| 6,011,985 A | 1/2000 | Athan et al. | | 6,263,223 B1 | 7/2001 | Sheperd et al. |
| 6,011,986 A | 1/2000 | Diab et al. | | 6,266,546 B1 | 7/2001 | Steuer et al. |
| 6,014,576 A | 1/2000 | Raley et al. | | 6,266,547 B1 | 7/2001 | Walker et al. |
| 6,018,673 A | 1/2000 | Chin et al. | | 6,272,363 B1 | 8/2001 | Casciani et al. |
| 6,018,674 A | 1/2000 | Aronow | | 6,278,522 B1 | 8/2001 | Lepper, Jr. et al. |
| 6,022,321 A | 2/2000 | Amano et al. | | 6,278,889 B1 * | 8/2001 | Robinson ..................... 600/322 |
| 6,023,541 A | 2/2000 | Merchant et al. | | 6,280,213 B1 | 8/2001 | Tobler et al. |
| 6,026,312 A | 2/2000 | Shemwell et al. | | 6,280,381 B1 | 8/2001 | Malin et al. |
| 6,026,314 A | 2/2000 | Amerov et al. | | 6,285,894 B1 | 9/2001 | Oppelt et al. |
| 6,031,603 A | 2/2000 | Fine et al. | | 6,285,895 B1 | 9/2001 | Ristolainen et al. |
| 6,035,223 A | 3/2000 | Baker, Jr. | | 6,285,896 B1 | 9/2001 | Tobler et al. |
| 6,036,642 A | 3/2000 | Diab et al. | | 6,298,252 B1 | 10/2001 | Kovach et al. |
| 6,041,247 A | 3/2000 | Weckstrom et al. | | 6,308,089 B1 | 10/2001 | von der Ruhr et al. |
| 6,044,283 A | 3/2000 | Fein et al. | | 6,312,393 B1 | 11/2001 | Abreu |
| 6,047,201 A | 4/2000 | Jackson, III | | 6,321,100 B1 | 11/2001 | Parker |
| 6,061,584 A | 5/2000 | Lovejoy et al. | | 6,330,468 B1 | 12/2001 | Scharf |
| 6,064,898 A | 5/2000 | Aldrich | | 6,334,065 B1 | 12/2001 | Al-Ali et al. |
| 6,064,899 A | 5/2000 | Fein et al. | | 6,339,715 B1 | 1/2002 | Bahr et al. |
| 6,067,462 A | 5/2000 | Diab et al. | | 6,343,223 B1 | 1/2002 | Chin et al. |
| 6,073,038 A | 6/2000 | Wang et al. | | 6,343,224 B1 | 1/2002 | Parker |
| 6,078,833 A | 6/2000 | Hueber | | 6,349,228 B1 | 2/2002 | Kiani et al. |
| 6,081,735 A | 6/2000 | Diab et al. | | 6,351,658 B1 | 2/2002 | Middleman et al. |
| 6,081,742 A | 6/2000 | Amano et al. | | 6,353,750 B1 | 3/2002 | Kimura et al. |
| 6,083,157 A | 7/2000 | Noller | | 6,356,774 B1 | 3/2002 | Bernstein et al. |
| 6,083,172 A | 7/2000 | Baker, Jr. et al. | | 6,360,113 B1 | 3/2002 | Dettling |
| 6,088,607 A | 7/2000 | Diab et al. | | 6,360,114 B1 | 3/2002 | Diab et al. |
| 6,094,592 A | 7/2000 | Yorkey et al. | | 6,361,501 B1 | 3/2002 | Amano et al. |
| 6,095,974 A | 8/2000 | Shemwell et al. | | 6,363,269 B1 | 3/2002 | Hanna et al. |
| 6,104,938 A | 8/2000 | Huiku et al. | | 6,370,408 B1 | 4/2002 | Merchant et al. |
| 6,112,107 A | 8/2000 | Hannula | | 6,370,409 B1 | 4/2002 | Chung et al. |
| 6,113,541 A | 9/2000 | Dias et al. | | 6,374,129 B1 | 4/2002 | Chin et al. |
| 6,115,621 A | 9/2000 | Chin | | 6,377,829 B1 | 4/2002 | Al-Ali |
| 6,120,460 A | 9/2000 | Abreu | | 6,381,479 B1 | 4/2002 | Norris |
| 6,122,535 A | 9/2000 | Kaestle et al. | | 6,381,480 B1 | 4/2002 | Stoddar et al. |
| 6,133,994 A | 10/2000 | Mathews et al. | | 6,385,471 B1 | 5/2002 | Mortz |
| 6,134,460 A | 10/2000 | Chance | | 6,385,821 B1 | 5/2002 | Modgil et al. |
| 6,135,952 A | 10/2000 | Coetzee | | 6,388,240 B2 | 5/2002 | Schulz et al. |
| 6,144,444 A | 11/2000 | Haworth et al. | | 6,393,310 B1 | 5/2002 | Kuenster |
| 6,144,867 A | 11/2000 | Walker et al. | | 6,397,091 B2 | 5/2002 | Diab et al. |
| 6,144,868 A | 11/2000 | Parker | | 6,397,092 B1 | 5/2002 | Norris et al. |
| 6,149,481 A | 11/2000 | Wang et al. | | 6,397,093 B1 | 5/2002 | Aldrich |
| 6,150,951 A | 11/2000 | Olejniczak | | 6,400,971 B1 | 6/2002 | Finarov et al. |
| 6,151,107 A | 11/2000 | Schöllerman et al. | | 6,400,972 B1 | 6/2002 | Fine |
| 6,151,518 A | 11/2000 | Hayashi | | 6,402,690 B1 | 6/2002 | Rhee et al. |
| 6,152,754 A | 11/2000 | Gerhardt et al. | | 6,408,198 B1 | 6/2002 | Hanna et al. |

| Patent | Date | Inventor |
|---|---|---|
| 6,411,832 B1 | 6/2002 | Guthermann |
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,487,439 B1 | 11/2002 | Skladnev et al. |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,544,193 B2 | 4/2003 | Abreu |
| 6,546,267 B1 | 4/2003 | Sugiura et al. |
| 6,549,795 B1 | 4/2003 | Chance |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,573,991 B1 | 6/2003 | Debreczeny et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,622,095 B2 | 9/2003 | Kobayashi et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,690,958 B1 | 2/2004 | Walker et al. |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,048 B1 | 3/2004 | Chance |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,785,568 B2 | 8/2004 | Chance |

| Patent No. | Date | Inventor |
|---|---|---|
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,949,081 B1 | 9/2005 | Chance |
| 6,950,687 B2 | 9/2005 | Al-Ali |
| 6,961,598 B2 | 11/2005 | Diab |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boas et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,252 B1 | 7/2006 | Debreczeny et al. |
| 7,079,880 B2 | 7/2006 | Stetson |
| 7,085,597 B2 | 8/2006 | Fein et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,236,881 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,257,433 B2 | 8/2007 | Takamura et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,283,242 B2 | 10/2007 | Thornton |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,319,894 B2 | 1/2008 | Higgins |
| 7,330,746 B2 | 2/2008 | Demuth et al. |
| 7,415,298 B2 | 8/2008 | Casciani et al. |
| 7,424,317 B2 | 9/2008 | Parker et al. |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2001/0051767 A1 | 12/2001 | Williams et al. |
| 2002/0026106 A1 | 2/2002 | Khalil et al. |
| 2002/0026109 A1 | 2/2002 | Diab et al. |
| 2002/0028990 A1 | 3/2002 | Sheperd et al. |
| 2002/0035318 A1 | 3/2002 | Mannheimer et al. |
| 2002/0038078 A1 | 3/2002 | Ito |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0068859 A1 | 6/2002 | Knopp |
| 2002/0098120 A1* | 7/2002 | Blazewicz et al. .......... 422/82.07 |
| 2002/0111748 A1 | 8/2002 | Kobayashi et al. |
| 2002/0128544 A1 | 9/2002 | Diab et al. |
| 2002/0133067 A1 | 9/2002 | Jackson, III |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2002/0198443 A1 | 12/2002 | Ting |
| 2003/0018243 A1 | 1/2003 | Gerhardt et al. |
| 2003/0023140 A1 | 1/2003 | Chance |
| 2003/0036690 A1 | 2/2003 | Geddes et al. |
| 2003/0045785 A1 | 3/2003 | Diab et al. |
| 2003/0055324 A1 | 3/2003 | Wasserman |
| 2003/0060693 A1 | 3/2003 | Monfre et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0139687 A1 | 7/2003 | Abreu |
| 2003/0144584 A1 | 7/2003 | Mendelson |

| | | | | | | |
|---|---|---|---|---|---|---|
| 2003/0162414 A1 | 8/2003 | Schulz et al. | | 2005/0010092 A1 | 1/2005 | Weber et al. |
| 2003/0171662 A1 | 9/2003 | O'Connor et al. | | 2005/0020887 A1 | 1/2005 | Goldberg |
| 2003/0176776 A1 | 9/2003 | Huiku | | 2005/0020894 A1 | 1/2005 | Norris et al. |
| 2003/0181799 A1 | 9/2003 | Lindekugel et al. | | 2005/0033128 A1 | 2/2005 | Ali et al. |
| 2003/0187337 A1 | 10/2003 | Tarassenko et al. | | 2005/0033129 A1 | 2/2005 | Edgar, Jr. et al. |
| 2003/0195402 A1 | 10/2003 | Fein et al. | | 2005/0043599 A1 | 2/2005 | O'Mara |
| 2003/0197679 A1 | 10/2003 | Ali et al. | | 2005/0043600 A1 | 2/2005 | Diab et al. |
| 2003/0212316 A1 | 11/2003 | Leiden et al. | | 2005/0049470 A1 | 3/2005 | Terry |
| 2003/0220548 A1 | 11/2003 | Schmitt | | 2005/0049471 A1 | 3/2005 | Aceti |
| 2003/0220576 A1 | 11/2003 | Diab | | 2005/0075550 A1 | 4/2005 | Lindekugel |
| 2003/0225323 A1 | 12/2003 | Kiani et al. | | 2005/0080323 A1 | 4/2005 | Kato |
| 2003/0225337 A1 | 12/2003 | Scharf et al. | | 2005/0101850 A1 | 5/2005 | Parker |
| 2003/0236452 A1 | 12/2003 | Melker et al. | | 2005/0113656 A1 | 5/2005 | Chance |
| 2003/0236647 A1 | 12/2003 | Yoon et al. | | 2005/0168722 A1 | 8/2005 | Forstner et al. |
| 2004/0006261 A1 | 1/2004 | Swedlow et al. | | 2005/0177034 A1 | 8/2005 | Beaumont |
| 2004/0010188 A1 | 1/2004 | Wasserman et al. | | 2005/0192488 A1 | 9/2005 | Bryenton et al. |
| 2004/0024297 A1 | 2/2004 | Chen et al. | | 2005/0197548 A1 | 9/2005 | Dietiker |
| 2004/0024326 A1 | 2/2004 | Yeo et al. | | 2005/0203357 A1 | 9/2005 | Debreczeny et al. |
| 2004/0034293 A1 | 2/2004 | Kimball | | 2005/0228248 A1 | 10/2005 | Dietiker |
| 2004/0039272 A1 | 2/2004 | Abdul-Hafiz et al. | | 2005/0228253 A1 | 10/2005 | Debreczeny |
| 2004/0039273 A1 | 2/2004 | Terry | | 2005/0267346 A1 | 12/2005 | Faber et al. |
| 2004/0054269 A1 | 3/2004 | Rantala et al. | | 2005/0277819 A1 | 12/2005 | Kiani et al. |
| 2004/0054270 A1 | 3/2004 | Pewzner et al. | | 2005/0283059 A1 | 12/2005 | Iyer et al. |
| 2004/0054291 A1 | 3/2004 | Schulz et al. | | 2006/0009688 A1 | 1/2006 | Lamego et al. |
| 2004/0059209 A1 | 3/2004 | Al-Ali et al. | | 2006/0015021 A1 | 1/2006 | Cheng |
| 2004/0059210 A1 | 3/2004 | Stetson | | 2006/0020181 A1 | 1/2006 | Schmitt |
| 2004/0064020 A1 | 4/2004 | Diab et al. | | 2006/0025660 A1 | 2/2006 | Swedlow et al. |
| 2004/0068164 A1 | 4/2004 | Diab et al. | | 2006/0030763 A1 | 2/2006 | Mannheimer et al. |
| 2004/0087846 A1 | 5/2004 | Wasserman | | 2006/0052680 A1 | 3/2006 | Diab |
| 2004/0092805 A1 | 5/2004 | Yarita | | 2006/0058594 A1 | 3/2006 | Ishizuka et al. |
| 2004/0097797 A1 | 5/2004 | Porges et al. | | 2006/0058683 A1 | 3/2006 | Chance |
| 2004/0098009 A1 | 5/2004 | Boecker et al. | | 2006/0064024 A1 | 3/2006 | Schnall |
| 2004/0107065 A1 | 6/2004 | Al-Ali et al. | | 2006/0084852 A1 | 4/2006 | Mason et al. |
| 2004/0116788 A1 | 6/2004 | Chernoguz et al. | | 2006/0084864 A1 | 4/2006 | Schmitt et al. |
| 2004/0116789 A1 | 6/2004 | Boaz et al. | | 2006/0089547 A1 | 4/2006 | Sarussi |
| 2004/0117891 A1 | 6/2004 | Hannula et al. | | 2006/0106294 A1 | 5/2006 | Maser et al. |
| 2004/0122300 A1 | 6/2004 | Boas et al. | | 2006/0122520 A1* | 6/2006 | Banet et al. .......... 600/503 |
| 2004/0122302 A1 | 6/2004 | Mason et al. | | 2006/0189861 A1 | 8/2006 | Chen et al. |
| 2004/0127779 A1 | 7/2004 | Steuer et al. | | 2006/0195028 A1 | 8/2006 | Hannula et al. |
| 2004/0133087 A1 | 7/2004 | Ali et al. | | 2006/0224058 A1 | 10/2006 | Mannheimer |
| 2004/0133088 A1 | 7/2004 | Al-Ali et al. | | 2006/0247501 A1 | 11/2006 | Ali |
| 2004/0138538 A1 | 7/2004 | Stetson | | 2006/0258921 A1 | 11/2006 | Addison et al. |
| 2004/0138540 A1 | 7/2004 | Baker, Jr. et al. | | 2007/0032710 A1 | 2/2007 | Raridan et al. |
| 2004/0143172 A1 | 7/2004 | Fudge et al. | | 2007/0032712 A1 | 2/2007 | Raridan et al. |
| 2004/0147821 A1 | 7/2004 | Al-Ali et al. | | 2007/0032715 A1 | 2/2007 | Eghbal et al. |
| 2004/0147822 A1 | 7/2004 | Al-Ali et al. | | 2007/0060809 A1 | 3/2007 | Higgins |
| 2004/0147823 A1 | 7/2004 | Kiani et al. | | 2007/0073126 A1 | 3/2007 | Raridan, Jr. |
| 2004/0147824 A1 | 7/2004 | Diab et al. | | 2007/0129616 A1 | 6/2007 | Rantala |
| 2004/0152965 A1 | 8/2004 | Diab et al. | | 2007/0282178 A1 | 12/2007 | Scholler et al. |
| 2004/0158134 A1 | 8/2004 | Diab et al. | | 2007/0282183 A1 | 12/2007 | Scholler et al. |
| 2004/0158135 A1 | 8/2004 | Baker, Jr. et al. | | 2008/0108887 A1 | 5/2008 | Higgins |
| 2004/0162472 A1 | 8/2004 | Berson et al. | | 2008/0139908 A1 | 6/2008 | Kurth |
| 2004/0171920 A1 | 9/2004 | Mannheimer et al. | | 2008/0214911 A1 | 9/2008 | Forstner |
| 2004/0171948 A1 | 9/2004 | Terry | | | | |
| 2004/0176670 A1 | 9/2004 | Takamura et al. | | FOREIGN PATENT DOCUMENTS | | |
| 2004/0176671 A1 | 9/2004 | Fine et al. | | CN | 1540314 | 10/2004 |
| 2004/0181133 A1 | 9/2004 | Al-Ali et al. | | CN | 1223843 | 11/2004 |
| 2004/0181134 A1 | 9/2004 | Baker, Jr. et al. | | CN | 2691489 | 4/2005 |
| 2004/0186358 A1 | 9/2004 | Chernow et al. | | EP | 0194105 | 9/1986 |
| 2004/0199063 A1 | 10/2004 | O'Neil et al. | | EP | 0497021 | 8/1992 |
| 2004/0204636 A1 | 10/2004 | Diab et al. | | EP | 0630203 | 12/1994 |
| 2004/0204637 A1 | 10/2004 | Diab et al. | | EP | 1346683 A | 9/2003 |
| 2004/0204638 A1 | 10/2004 | Diab et al. | | EP | 1491135 | 12/2004 |
| 2004/0204639 A1 | 10/2004 | Casciani et al. | | JP | 3245042 | 10/1991 |
| 2004/0204865 A1 | 10/2004 | Lee et al. | | JP | 4038280 | 3/1992 |
| 2004/0210146 A1 | 10/2004 | Diab et al. | | JP | 4191642 | 7/1992 |
| 2004/0215069 A1 | 10/2004 | Mannheimer | | JP | 5049625 | 3/1993 |
| 2004/0230106 A1 | 11/2004 | Schmitt et al. | | JP | 6014906 | 1/1994 |
| 2004/0230107 A1 | 11/2004 | Asada et al. | | JP | 6154177 | 6/1994 |
| 2004/0230108 A1 | 11/2004 | Melker et al. | | JP | 3939782 | 1/1998 |
| 2004/0236196 A1 | 11/2004 | Diab et al. | | JP | 10216115 | 8/1998 |
| 2004/0242980 A1 | 12/2004 | Kiani et al. | | JP | 10337282 | 12/1998 |
| 2004/0249252 A1 | 12/2004 | Fine et al. | | JP | 11019074 | 1/1999 |
| 2004/0257557 A1 | 12/2004 | Block et al. | | JP | 2002224088 | 8/2002 |
| 2004/0260161 A1 | 12/2004 | Melker et al. | | JP | 2003194714 | 7/2003 |
| 2004/0267103 A1 | 12/2004 | Li et al. | | JP | 2004148069 | 5/2004 |
| 2004/0267104 A1 | 12/2004 | Hannula et al. | | JP | 2004148070 | 5/2004 |
| 2004/0267140 A1 | 12/2004 | Ito et al. | | JP | 2004166775 | 6/2004 |
| 2005/0004479 A1 | 1/2005 | Townsend et al. | | JP | 3944448 | 7/2004 |

| | | |
|---|---|---|
| JP | 2004248820 | 9/2004 |
| JP | 2004290544 | 10/2004 |
| JP | 2004329607 | 11/2004 |
| JP | 2004351107 | 12/2004 |
| JP | 2005095581 | 4/2005 |
| JP | 2005278758 | 10/2005 |
| JP | 2006061566 | 3/2006 |
| JP | 2006075354 | 3/2006 |
| JP | 2006081703 | 3/2006 |
| JP | 2006122693 | 5/2006 |
| JP | 2006212161 | 8/2006 |
| JP | 2006239267 | 9/2006 |
| JP | 2006297125 | 11/2006 |
| JP | 2006325766 | 12/2006 |
| JP | 2006326153 | 12/2006 |
| JP | 2007020836 | 2/2007 |
| JP | 2007117641 | 5/2007 |
| JP | 2007167184 | 7/2007 |
| JP | 2007190122 | 8/2007 |
| JP | 2007330708 | 12/2007 |
| WO | WO 93/16629 | 9/1993 |
| WO | WO 94/03102 A | 2/1994 |
| WO | WO9101678 | 2/1994 |
| WO | WO9423643 | 10/1994 |
| WO | WO9512349 | 5/1995 |
| WO | 9749330 A | 12/1997 |
| WO | WO9749330 | 12/1997 |
| WO | WO9817174 | 4/1998 |
| WO | WO9857577 | 12/1998 |
| WO | WO9947039 | 9/1999 |
| WO | WO03039326 | 5/2003 |
| WO | WO2005/007215 | 1/2005 |
| WO | WO2005/099568 | 10/2005 |
| WO | WO2006124696 | 11/2006 |
| WO | WO2008039187 | 4/2008 |

OTHER PUBLICATIONS

Ferrell, T.L., et al.; "Medical Telesensors," *SPIE*, vol. 3253, pp. 193-198 (1998).

Lutter, N., et al.; "Comparison of Different Evaluation Methods for a Multi-wavelength Pulse Oximeter," *Biomedizinische Technik*, vol. 43, (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Aoyagi, T., et al.; "Pulse Oximeters: background, present and future," *Neonatal Care*, vol. 13, No. 7, pp. 21-27 (2000) (Article in Japanese—contains English summary of article).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Lopez-Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

\* cited by examiner

SYMMETRIC LED ARRAY FOR PULSE OXIMETRY

BACKGROUND

1. Field of Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood oxygen saturation of hemoglobin in arterial blood, the volume of individual blood pulsations supplying the tissue, and/or the rate of blood pulsations corresponding to each heart beat of a patient. In fact, the "pulse" in pulse oximetry refers to the time varying amount of arterial blood in the tissue during each cardiac cycle.

Pulse oximeters typically utilize a non-invasive sensor that transmits or reflects electromagnetic radiation, such as light, through a patient's tissue and that photoelectrically detects the absorption and scattering of the transmitted or reflected light in such tissue. One or more of the above physiological characteristics may then be calculated based upon the amount of light absorbed and scattered. More specifically, the light passed through or reflected from the tissue is typically selected to be of one or more wavelengths that may be absorbed and scattered by the blood in an amount correlative to the amount of blood constituent present in the tissue. The measured amount of light absorbed and scattered may then be used to estimate the amount of blood constituent in the tissue using various algorithms.

Certain events can create error in these measurements. For example, pulse oximetry measurements may be sensitive to movement of the sensor relative to the patient's tissue, and various types of motion may cause artifacts that may obscure the blood constituent signal. Specifically, motion artifacts may be caused by moving a sensor in relation to the tissue, increasing or decreasing the physical distance between emitters and detectors in a sensor, changing the angles of incidents and interfaces probed by the light, directing the optical path through different amounts or types of tissue, and by expanding, compressing, or otherwise altering tissue near a sensor.

Pulse oximetry may utilize light sources that emit in at least two different or spectral regions, one that emits in the red region (typically about 660 nm) and one in the near infrared region (typically about 890-940 nm). Typically, LEDs are used as light sources and are held in close proximity, i.e., optically coupled, to a tissue location being probed. In the context of pulse oximetry, optical coupling refers to a relationship between the sensor and the patient, permitting the sensor to transmit light into the patient's blood profused tissue and permitting a portion of the light to return to the sensor after passing through or reflecting from within the tissue. The quality of the optical coupling of the emitters and detectors is related to the amount of light that actually enters the patient's tissue and the portion of the light received by the sensor that passes through the patient's blood profused tissue. As described earlier, motion and/or the application of excessive pressure can have the effect of changing the relative optical coupling efficiency of the light sources and the detector. Even when two LEDs are mounted side by side, motion induced changes in optical efficiency have resulted in distortions of the photoplethysmographs produced by the two LEDs. The result of poor coupling, therefore, is a decrease in the accuracy of the sensor.

Homogenizing the light sources using optical coupling devices is one way of mitigating the effect of motion-induced changes in optical efficiency on the accuracy of a pulse oximeter. Such techniques, however, generally require careful optical alignment, tend to be expensive, or reduce the optical coupling efficiency into the tissue.

Sensor-to-sensor spectral variation of light sources used for oximeter sensors may also affect a pulse oximeter's accuracy. Because hemoglobin ($HbO_2$ and $HHb$) spectra vary more rapidly as a function of wavelength at approximately 660 nm than at approximately 940 nm, the precise spectral content of the 660 nm light source is more critical. Current manufacturing processes used to produce 660 nm LEDs result in a wide distribution of spectral content, potentially necessitating modification of the calibration model according to actual spectral content of the 660 nm source, thus adding cost to the system. Alternatively, choosing only LEDs that emit in a narrow wavelength range would result in low production yields and higher sensor cost. Thus, costs are incurred either by limiting the range of wavelengths to reduce the need for calibration, or by allowing for a wider spectral content and inserting calibration models.

SUMMARY

Certain aspects commensurate in scope with the originally claimed invention are set forth below. It should be understood that these aspects are presented merely to provide the reader with a brief summary of certain forms the invention might take and, these aspects are not intended to limit the scope of the invention. Indeed, the invention may encompass a variety of aspects that may not be set forth below.

In accordance with one aspect of the present invention a sensor for pulse oximeter systems is provided. The sensor comprises a first source of electromagnetic radiation configured to operate at a first wavelength, a second source of electromagnetic radiation configured to operate at a second wavelength and a third source of electromagnetic radiation configured to operate at a third wavelength. The first and third sources of electromagnetic radiation overlap at their half power level or greater and correspond to a center wavelength in the range of 650 to 670 nm. A photodetector is configured to receive electromagnetic radiation from blood-perfused tissue irradiated by the first, second and third sources of electromagnetic radiation.

In accordance with another aspect of the present invention there is provided a sensor comprising a first source of electromagnetic radiation configured to operate at a first wavelength, a second source of electromagnetic radiation configured to operate at a second wavelength and a third source of electromagnetic radiation configured to operate at a third wavelength. A photodetector is configured to receive electromagnetic radiation from the blood-perfused tissue, and the first and third sources of electromagnetic radiation are symmetrically disposed spatially relative to the photodetector.

In accordance with yet another aspect of the present invention a sensor comprising a first light emitting diode configured to emit radiation having a maximum intensity corresponding to wavelengths in a red region of the electromagnetic spectrum. The sensor also comprises a second LED configured to operate in the near-infrared region of the electromagnetic spectrum and a third LED configured to operate in the red region of the electromagnetic spectrum. The third LED has a maximum intensity at a wavelength greater than 650 nm and greater than the wavelength at which the first LED has a maximum. The first LED and third LED are spectrally symmetrical with respect to a center wavelength in the range 650 to 670 nm.

BRIEF DESCRIPTION OF THE DRAWINGS

Advantages of the invention may become apparent upon reading the following detailed description and upon reference to the drawings, in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve developer's specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with aspects of the present invention, techniques are disclosed for reducing the susceptibility of pulse oximeters to error caused by motion or spectral variation of light sources. Additionally, techniques are disclosed that allow for the operation of pulse oximetry systems with a broad spectral content and, potentially, without calibration.

Figure 1:
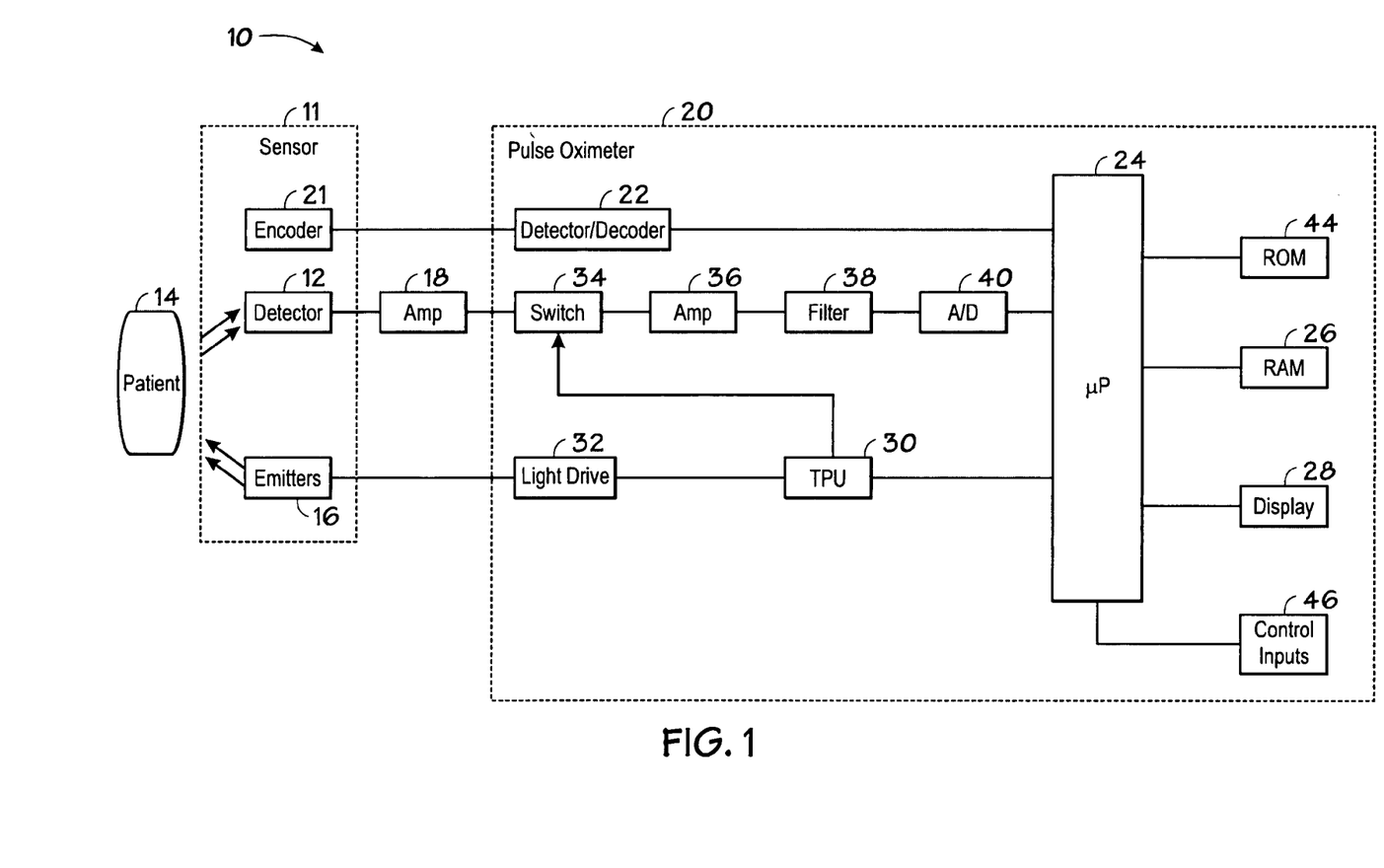
FIG. 1 illustrates a block diagram of a pulse oximeter system in accordance with an exemplary embodiment of the present invention.

Turning to FIG. 1, a block diagram of a pulse oximeter system in accordance with an exemplary embodiment of the present invention is illustrated and generally designated by the reference numeral 10. The pulse oximeter system 10 includes a sensor 11 having a detector 12 which receives electromagnetic radiation from the blood perfused tissue of a patient 14. The electromagnetic radiation originates from emitters 16. A photoelectric current is generated when the electromagnetic radiation scattered and absorbed by the tissue arrives at the detector 12. The current signal produced by the detector 12 is amplified by an amplifier 18 prior to being sent to the pulse oximeter 20.

The emitters 16 may be one or more LEDs configured to emit in the red and near infrared regions of the electromagnetic spectrum. As will be explained in greater detail below, the emitters 16 may be oriented to provide spatial symmetry about an axis. Additionally, the emitters 16 may be spectrally symmetrical about a central wavelength to eliminate the use of a spectrum calibration model.

In addition to providing a signal corresponding to the amount of electromagnetic radiation scattered and absorbed by the tissue, the sensor 11 may also be configured to provide calibration data to the pulse oximeter 20 via an encoder 21. Pulse oximetry algorithms typically use coefficients indicative of certain parameters of a particular system. The particular set of coefficients chosen for a particular set of wavelength spectra is determined by the value indicated by encoder 21 corresponding to a particular light source in a particular sensor. In one configuration, multiple resistor values may be assigned to select different sets of coefficients. In this instance, the encoder 21 may include one or a plurality of resistor values and a detector 22 located in the pulse oximeter 20 reads the resistor values and selects coefficients from a stored table. Alternatively, the encoder 21 may be a memory that either stores the wavelength information or the coefficients. Thus, the encoder 21 and the decoder 22 allow the pulse oximeter 20 to be calibrated according to the particular wavelengths of the emitters 16.

In an exemplary embodiment, the pulse oximeter 20 includes a microprocessor 24 that processes data received from the sensor 11 to compute various physiological parameters. The pulse oximeter 20 may also include a random access memory (RAM) 26 for storing data and an output display 28 for displaying computed parameters. A time processing unit (TPU) 30 may be provided to control the timing of the pulse oximeter 20. The TPU may be coupled to light drive circuitry 32 and a switch 34. The light drive circuitry 32 controls light emissions of the emitters 16, and the switch 34 receives and controls the gating-in of the amplified signals from the detector 12. The received signals are passed from the switch 34 through a second amplifier 36, a filter 38, and an analog-to-digital converter (A/D) 40, before arriving at the microprocessor 24.

Upon receiving the signals, the microprocessor 24 calculates the oxygen saturation and other physiological parameters. In calculating the physiological parameters, the microprocessor 24 uses algorithms stored on a read-only memory (ROM) 44 and data stored in the RAM 26. As discussed above, the algorithms typically use coefficients which correspond to the wavelengths of light used and calibrate the pulse oximeter 20 to the particular wavelengths being used. Implementation of spectral symmetry techniques may, however, eliminate such calibration.

The display 28 outputs the physiological parameters, such as oxygen saturation, calculated by the pulse oximeter 20. The block diagram of the pulse oximeter system 10 is exemplary, and it should be understood that various alternative configurations may be possible. For example, there may be multiple parallel paths of separate amplifiers, filters, and A/D converters for multiple light wavelengths or spectra received. Additionally, implementation of spectral symmetry techniques may obviate the encoder 21 and decoder 22.

Figure 2:
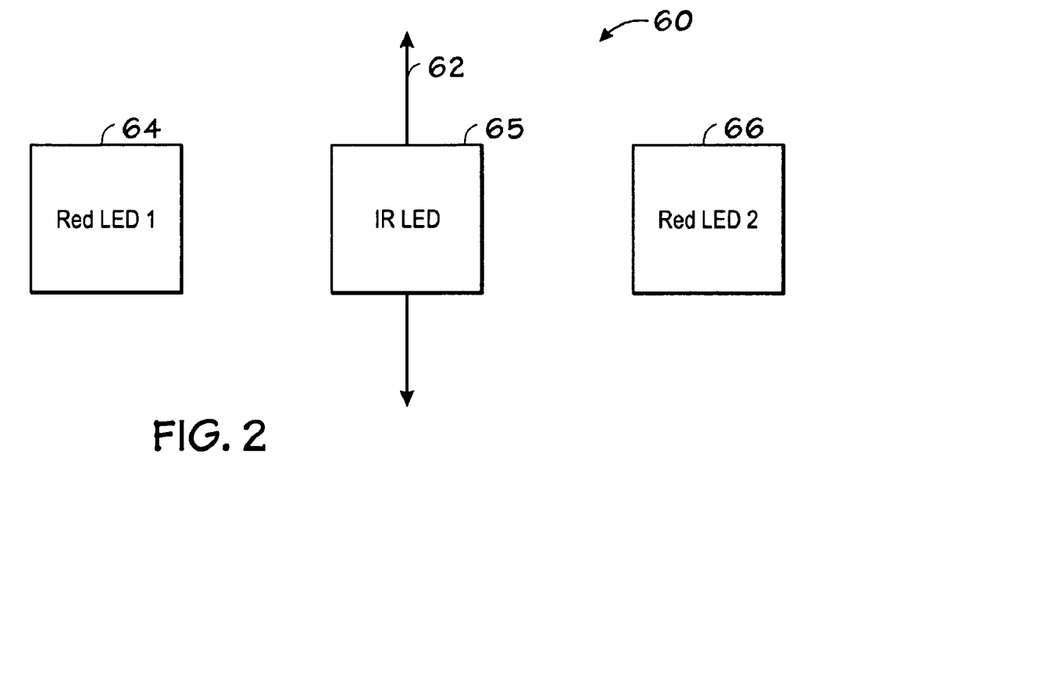
FIG. 2 illustrates spatial symmetry of the light sources in accordance with an exemplary embodiment of the present invention.

Spatial symmetry of the emitters 16 may provide a level of immunity against motion induced artifacts. FIG. 2 diagrammatically illustrates the emitter portion of a sensor having emitter LEDs 64, 65 and 66 symmetrically oriented relative to an axis 62 in accordance with an exemplary embodiment of the present invention. The first LED 64 is positioned on one side of the center LED 65, while the second LED 66 is positioned on the other side of the center LED 65. The axis 62 runs through the center of the center LED 65 and may represent the long axis of a patient's finger to which the LEDs may couple. The center LED 65 typically emits radiation in the infrared (IR) or near infrared (NMR) range, while the LEDs 64 and 66 have similar spectral outputs in the red range of approximately 600 to 800 nm to help ensure that any coupling issues that may occur due to movement of tissue relative to one LED may be compensated for by the other LED. For example, if the finger moves away from the LED 64, resulting in poor coupling with LED 64, the coupling of the finger with LED 66 may still exhibit good coupling or even improved coupling due to the movement.

As discussed above, pulse oximeters typically employ light sources that operate in the near infrared (NIR)/infrared (IR) and the red range of the electromagnetic spectrum. The different wavelengths of light generate different levels of current in the photodetector 12. As the red range produces a lower photocurrent in the photodetector 12, LEDs that emit in this range may be selected as the LEDs 64 and 66. Because the signal from the two LEDs 64 and 66 is additive, the signal-to-noise ratio of the sensor may be increased, thus, providing better readings.

Figure 3:
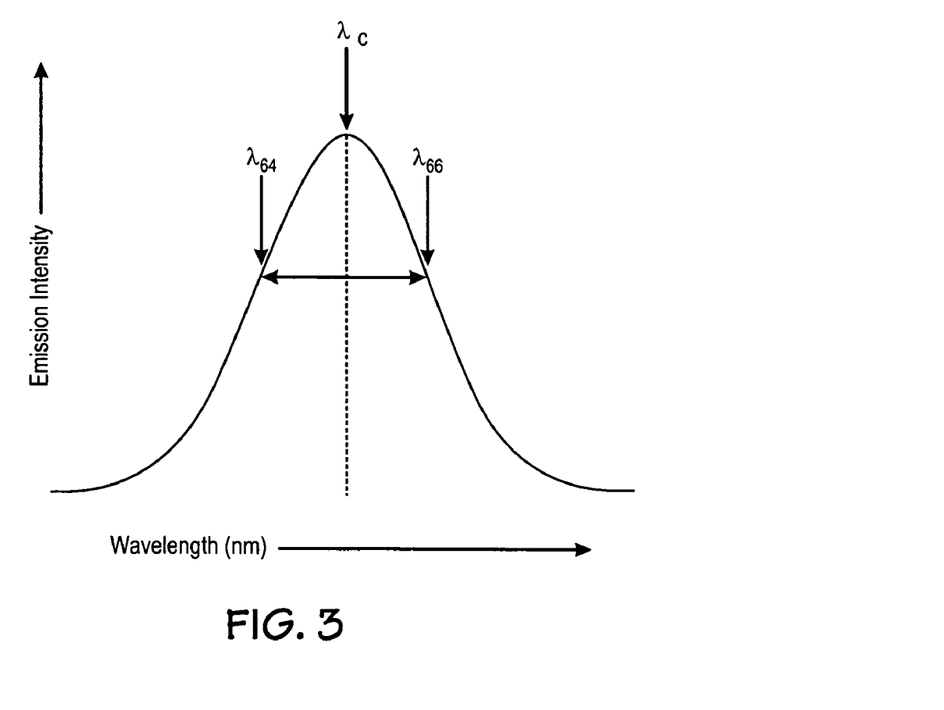
FIG. 3 illustrates an emission intensity plot of an emitter in accordance with an embodiment of the present invention.

In addition to the LEDs 64 and 66 being physically disposed in a symmetrical relationship, or in the alternative, the wavelengths of the LEDs 64 and 66 may be spectrally symmetrical with respect to one another. Spectral symmetry of the LEDs 64 and 66 may be implemented in combination with or independent from the spatial symmetry described above. FIG. 3 illustrates the emission intensity plot of an exemplary light emitter relative to the wavelength. Specifically, FIG. 3 illustrates that the emitter exhibits an emission intensity maximum at a center wavelength $\lambda_c$. The wavelengths $\lambda_{64}$ and $\lambda_{66}$ of the LEDs 64 and 66 are shown symmetrically disposed about the center wavelength $\lambda_c$. To provide spectral symmetry, two emitters are used that have emission intensity maxima at wavelengths equidistant in nanometers from the central wavelength $\lambda_c$ and on opposite spectral sides of the central wavelength $\lambda_c$, which may be selected to be 660 nm, for example. Specifically, the two wavelengths $\lambda_{64}$ and $\lambda_{66}$ are selected to have maxima at wavelengths that overlap at their half power level or greater at the center wavelength $\lambda_c$ such that when summed together they achieve a maximum intensity at the center wavelength $\lambda_c$, where the maximum intensity is greater than that of either LED 64 or LED 66 alone. For example, if the spectral bandwidth of the wavelengths $\lambda_c$, $\lambda_{64}$ and $\lambda_{66}$ are the same, two wavelengths $\lambda_{64}$ and $\lambda_{66}$ may be selected to correspond to the half power level or greater of the center wavelength $\lambda_c$. In other words, if the LED 64 has a maximum at 650 nm and the LED 66 has a maximum at 670 nm and the respective signals have not decreased beyond their half power level (−3 dB) at 660 nm, then the additive maximum of the LED 64 and LED 66 will occur at 660 nm. Thus, a stronger signal at the center wavelength, such as 660 nm may be achieved through spectral symmetry techniques.

Additionally, the use of spectral symmetry may eliminate the need for a calibration model. The hemoglobin ($HbO_2$ and HHb) spectra vary more rapidly as a function of wavelength at 660 nm than at 940 nm. Therefore, the precise spectral content of the red light source is more critical than that of the NIR/IR light source. Accurate predictions of oxygen saturation may be achieved by modification of the calibration model according to the spectral content of the particular red light sources being used, as discussed above. Spectral symmetry techniques, however, may be used to obviate calibration.

Figure 4:
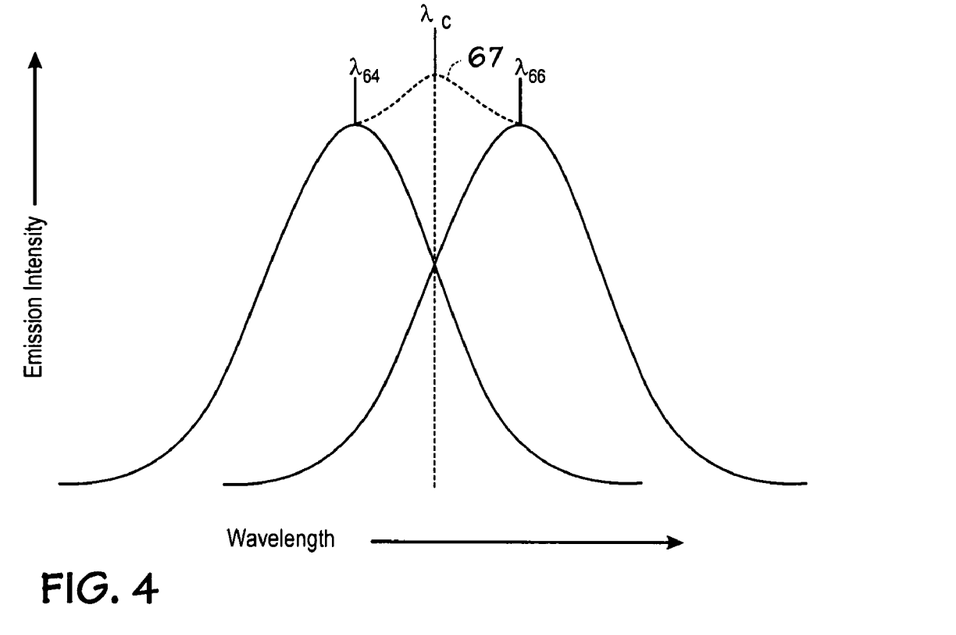
FIG. 4 illustrates the emission intensity plots of two emitters spectrally symmetrical relative to a central wavelength in accordance with embodiments of the present invention.

Referring to FIG. 4, the emission intensity of the two LEDs 64 and 66 having maxima at wavelengths $\lambda_{64}$ and $\lambda_{66}$, which are symmetrical about the center wavelength $\lambda_c$, e.g., approximately 660 nm, are illustrated. A maximum at the center wavelength, indicated by the dashed line 67, occurs due to the additive effects of the LEDs 64 and 66 emitting at the spectrally symmetrical wavelengths $\lambda_{64}$ and $\lambda_{66}$ which overlap at their half power level or greater. As discussed above, even though the LEDs 64 and 66 are not operating at the center wavelength $\lambda_c$, they may combine to create a maximum at the center wavelength $\lambda_c$. Thus, the technique of spectral symmetry may eliminate the wavelength specific calibration because the LEDs 64 and 66 are selected to be summed to create a maximum at the center wavelength $\lambda_c$ for which the pulse oximeter may already be programmed. It is inherent in this technique that the wavelength maximum, and not the spectral width of the light source, is used for the calibration of oximeter sensor light sources.

Furthermore, because the light sources are spectrally symmetrical and their intensities may add to have a maximum at the center wavelength $\lambda_c$, a wider range of light source spectra may be used. For example the range of currently allowed wavelengths for the 660 nm LEDs is approximately 650 nm to 670 nm. According to the techniques presented herein, however, it may be possible to use LEDs emitting outside the range of wavelengths between 650 and 670 nm. For example, a first LED can be selected to have an emission peak at a wavelength less than 670 µm, such as 648 nm, and second LED may be selected to have an emission peak at a wavelength greater than 650 µm, such as 672 nm. As long as signals from the first and second LEDs overlap at half power (−3 dB) or greater, a peak will be created by the overlap. Assuming that each LED has an equivalent spectral bandwidth, there will be a peak at 660 nm. Alternatively, the first LED can be selected to emit at 640 nm and the second LED can be selected to emit at 660 nm, thus providing spectral symmetry at 650 nm. Again, as long as the signals emitted from the first and second LEDs overlap at half power or greater at 650 nm, there will be a peak at 650 nm. The use of LEDs producing maximas at wavelength other than 660 nm, however, may require a calibration model to compensate for the lack of absorbance of hemoglobin at that particular wavelength. Additionally, the actual range of wavelengths that may be implemented may be limited by several factors, including the spectral bandwidth of the particular LEDs, the photosensitivity of the detector and limits on the spectrophotographic response of hemoglobin at wavelengths other than 660 nm. Specifically, if the LEDs only have a spectral bandwidth of twenty nanometers, the spectrally symmetrical LEDs can only have peaks twenty nanometers or less apart (i.e. ten nanometers from a desired center wavelength In an alternative exemplary embodiment, the implementation of the spectral symmetry techniques may produce a peak having a broader spectral bandwidth, rather than increasing the magnitude of the signal at the center wavelength. Specifically, the peak generated by summing the emitted wavelengths may not necessarily be greater than the peak generated by the individual LEDs 64 and 66 themselves. For example, the summed peak may have a magnitude approximately equivalent to the magnitude of peaks generated by the LEDs 64 and 66 alone. Accordingly, the intensity of the emissions across the spectra will be relatively flat between the wavelengths being used and at the center wavelength. The combined signal would provide a broader spectral bandwidth a the center wavelength, as the bandwidth extends from half power level on the blue side of the signal from LED 64 to the half power level on the red side of the LED 66.

Figure 5:
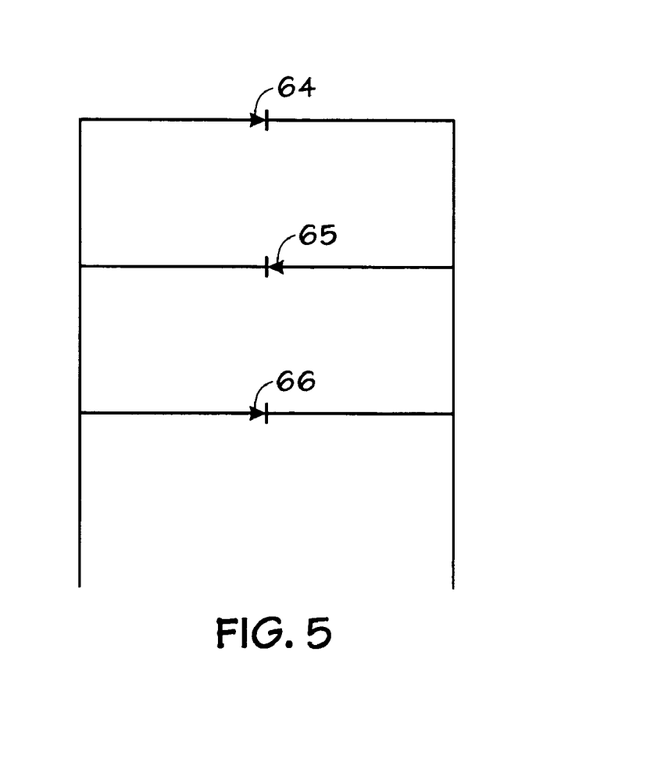
FIG. 5 illustrates an electrical configuration for LEDs of a pulse oximeter in accordance with an exemplary embodiment of the present invention.

An exemplary schematic of the electrical configuration of the multiple LEDs is illustrated in FIG. 5. The configuration of the LEDs may be the same regardless of whether the emitters provide spectral and/or spatial symmetry. The two LEDs 64 and 66 are electrically configured to emit light coincidentally, whereas the center LED 65 is configured to emit light while the LEDs 64 and 66 are off.

Figure 6:
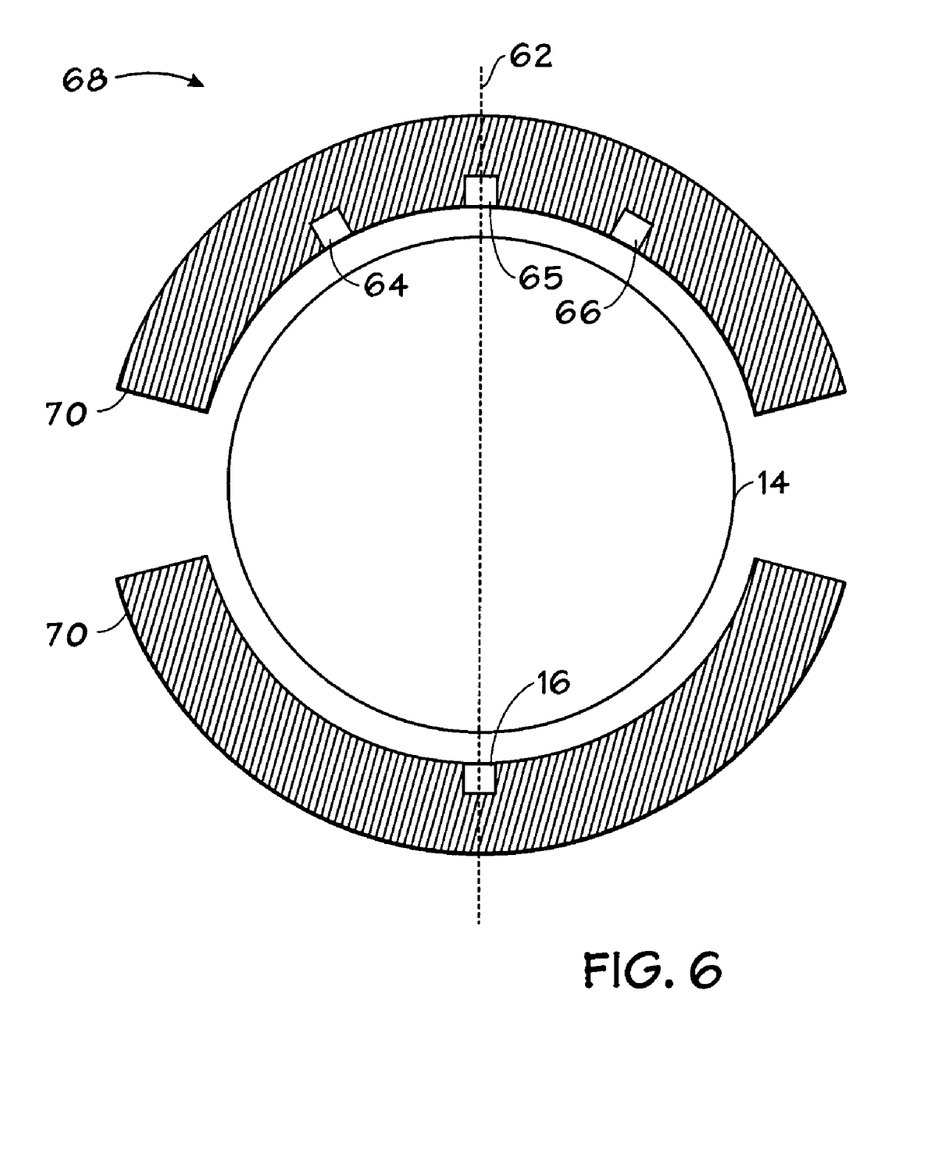
FIG. 6 illustrates a cross-sectional view of a pulse oximeter sensor in accordance with an exemplary embodiment of the present invention.

Turning to FIG. 6, a cross sectional view of a sensor in accordance with an exemplary embodiment of the present invention is illustrated and generally designated by the reference numeral 68. The cross sectional view of the sensor 68 shows a plurality of LEDs 64, 65 and 66 oriented about an axis 62. The center LED 65 and the detector 16 are bisected by the axis 62. The LEDs 64, 65, and 66 transmit electromagnetic radiation through a patient's tissue 14 which is detected by the detector 16. The housing 70 of the pulse oximeter 68 may be designed to limit movement of the patient 14 relative to the LEDs 64, 65, 66 and the detector 16, thus, reducing artifacts due to motion and poor coupling of the LEDs 64, 65, 66 and detector 16 to the patient. Specifically, the sensor 68 includes a curved shape about the patient's tissue 14 which permits rocking movement according to the curved shape of the housing 70, but which limits other movement. Movement such as rocking along the curvature of the housing 70 may be anti-correlated by the spatial symmetry of the sensor 68, thus reducing motion-induced artifacts.

As stated above, spatial symmetry techniques may be used in combination with or independent of the spectral symmetry technique. When implemented in a system that does not have spectral symmetry, it may be desirable to calibrate the pulse oximeter. When spectral symmetry techniques are implemented, the calibration may be unnecessary, as described above. In the event that spectral symmetry is implemented and the $\lambda_c$ is not 660 nm, it may still be desirable to calibrate according to the particular $\lambda_c$.

Several advantages are achieved by implementing the techniques described herein. For example, spatial symmetry may provide anti-correlation of motion-induced artifacts and increase the signal-to-noise ratio. Motion-induced artifacts are typically a result of changes in the coupling of the sensor with the patient's tissue. The spatial symmetry anti-correlates the motion induced artifacts by providing two LEDs symmetrically disposed about an axis of movement such that as the patient's tissue moves away from one LED the tissue couples with another LED operating at the same wavelength. Additionally, the summed signal from the symmetrically disposed LEDs may provide a stronger signal than a single LED to improve the signal-to-noise ratio for wavelengths which have a weaker photodetection effect.

The implementation of spectral symmetry may also provide a stronger signal at wavelengths which have a weaker photo detection effect. The combined emission strength of the two LEDs spectrally oriented about a central wavelength may provide a stronger signal for detection if each of LEDs have emission wavelengths which overlap above their half power level, as described above with reference to FIG. 4. Furthermore, the spectral symmetry allows the use of LEDs having a wider range of spectral content. Selecting light sources having maxima symmetrically disposed about a center wavelength in the range of 650 to 670 nm allows for a summed signal with a maximum within the 650 to 670 nm range. Thus, LEDs emitting outside of the 650 to 670 nm range may be used when paired with an LED having a peak emission wavelength symmetrically disposed about the center wavelength, as long as the spectra of the LEDs overlap at the center wavelength at their respective half power levels or greater.

Implementation of spectral symmetry may also allow for calibration-free sensors. Assuming that the wavelength maximum and not the spectral width of the LEDs is the most important aspect of the calibration, a center wavelength can be selected about which LED pairings are spectrally symmetrical. The pulse oximeter 20 can be set to operate according to a center wavelength, i.e. according to coefficients associated with the center wavelength, and no calibration is required. If variable spectral width due to the use of two LEDs is found to limit the accuracy of the measurement, an optical coating could be applied either to the light source or detector to limit the spectral width. For example, the detector could be coated with a material that passes light only with bands around 660 and 890 nm, but blocks the detection of light in all other spectral regions. In this way, the detected spectral band width would be primarily determined by the spectral width of the optical bandpass filter. This aspect of the invention would have the additional advantage of greatly limiting the influence of ambient light on the measured signal. Examples of suitable coatings include multilayer dielectric films and light-absorbing dyes.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of pulse oximetry, but these techniques may also be utilized for the measurement and/or analysis of other blood or tissue constituents. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts.

What is claimed is:

1. A sensor for pulse oximeter systems comprising:
   a first source of electromagnetic radiation configured to emit electromagnetic radiation at approximately a first center wavelength;
   a second source of electromagnetic radiation configured to emit electromagnetic radiation at approximately a second center wavelength, different from the first center wavelength;
   a third source of electromagnetic radiation configured to emit electromagnetic radiation at approximately a third center wavelength, different from the first and second center wavelengths, wherein the first center wavelength being less than a desired aggregate center wavelength, the third center wavelength being greater than the desired aggregate center wavelength, and the emission spectra of the first and third sources of electromagnetic radiation overlap at a half power level or greater of their respective emission maxima, the addition of the spectra causing a peak generally corresponding to the desired aggregate center wavelength; and a photodetector configured to receive electromagnetic radiation from blood-perfused tissue irradiated by the first, second and third sources of electromagnetic radiation.

2. The sensor of claim 1, wherein the first and third sources of electromagnetic radiation are about spectrally equidistant from the desired aggregate center wavelength.

3. The sensor of claim 1, wherein the photodetector is coated with a material that limits the spectral bandwidth of detected light.

4. The sensor of claim 3, wherein the material comprises a multilayer dielectric film.

5. The sensor of claim 3, wherein the material comprises a light-absorbing dye.

6. The sensor of claim 1, wherein at least one of the sources is coated with a material that limits the spectral bandwidth of the emitted electromagnetic radiation.

7. The sensor of claim 6, wherein the material comprises a multilayer dielectric film.

8. The sensor of claim 6, wherein the material comprises a light-absorbing dye.

9. The sensor of claim 1, comprising a curved housing configured to be disposed about a patient's finger, wherein the first, second and third sources are coupled to the curved housing and directed radially inward, the second source is positioned between the first and third sources along a circumference of the curved housing, and the photodetector is positioned generally opposite from the second source along the circumference of the curved housing.

10. The sensor of claim 1, wherein the first and third center wavelengths are within the red region of the electromagnetic spectrum, and the second center wavelength is within the infrared or near-infrared region of the electromagnetic spectrum.

11. The sensor of claim 1, wherein a magnitude of the desired aggregate center wavelength is greater than a magnitude of the first center wavelength, and greater than a magnitude of the third center wavelength.

12. The sensor of claim 1, wherein the desired aggregate center wavelength is about 660 nm.

13. The sensor of claim 12, wherein the first center wavelength is within a range of 650 to 659 nm, and the second center wavelength is within a range of 661 to 670 nm.

14. A system for determining physiological parameters comprising:
 a sensor comprising:
  a first light emitting diode (LED) configured to emit radiation in the red region of the electromagnetic spectrum, the first LED having a first peak emission at less than a desired aggregate center wavelength;
  a second LED configured to operate in the infrared or near-infrared region of the electromagnetic spectrum;
  a third LED configured to operate in the red region of the electromagnetic spectrum, the third LED having a second peak emission at greater than the desired aggregate center wavelength wherein the first and second peak emissions are generally symmetrically disposed about the desired aggregate center wavelength; and
  a photodetector configured to generate a signal corresponding to received electromagnetic radiation from blood-perfused tissue irradiated by the first, second and third LEDs; and
 a pulse oximeter configured to compute physiological parameters based on the signal generated by the photodetector.

15. The system of claim 14, comprising a curved housing configured to be disposed about a patient's finger, wherein the first, second and third LEDs are coupled to the curved housing and directed radially inward, the second LED is positioned between the first and third LEDs along a circumference of the curved housing, and the photodetector is positioned generally opposite from the second LED along the circumference of the curved housing.

16. The system of claim 15, wherein the curved housing is configured to allow optical coupling of the patient's finger with the first, second and third LEDs, and the photodetector.

17. The system of claim 15, wherein the curved housing is configured to inhibit axial movement of the patient's finger.

18. The system of claim 14, wherein the desired aggregate center wavelength is within a range of 650 to 670 nm.

19. The system of claim 14, wherein the first peak emission is within a range of 650 to 659 nm, and the second peak emission is within a range of 661 to 670 nm.

20. A method for determining physiological parameters using a pulse oximeter comprising:
 transmitting electromagnetic radiation from a first light emitting diode (LED), a second LED and a third LED, wherein the first and third LEDs operate concurrently, the first LED is configured to emit electromagnetic radiation at a first center wavelength, the second LED is configured to emit electromagnetic radiation at a second center wavelength, different from the first center wavelength, the third LED is configured to emit electromagnetic radiation at a third center wavelength, different from the first and second center wavelengths, the first center wavelength is less than a desired aggregate center wavelength, the third center wavelength is greater than the desired aggregate center wavelength, and the emission spectra of the first and third LEDs overlap at greater than or equal to a half power level of their respective emission spectra causing a peak corresponding to the desired aggregate center wavelength;
 generating a photoelectrical signal corresponding to the electromagnetic radiation from the first, second and third LEDs; and
 computing physiological parameters based on the photoelectrical signal.

* * * * *